United States Patent [19]

Katsumata et al.

[11] Patent Number: 4,681,847

[45] Date of Patent: Jul. 21, 1987

[54] NOVEL LYSOZYME-SENSITIVE MICROORGANISM

[75] Inventors: Ryoichi Katsumata, Machida; Tetsuo Oka, Yokohama; Akira Furuya, Kawasaki, all of Japan

[73] Assignee: Kyowa Hakko Kogyo Co., Ltd., Tokyo, Japan

[21] Appl. No.: 695,574

[22] Filed: Jan. 28, 1985

Related U.S. Application Data

[63] Continuation of Ser. No. 372,129, Apr. 27, 1982, abandoned.

[30] Foreign Application Priority Data

Apr. 30, 1981 [JP] Japan .................................. 56-65777
Sep. 25, 1981 [JP] Japan ................................ 56-151464

[51] Int. Cl.$^4$ ..................... C12N 15/00; C12N 9/36; C12N 1/20; C12N 1/00; C12N 1/06; C12P 21/00; C12P 19/34; C12R 1/13; C12R 1/15
[52] U.S. Cl. ................................. 435/172.3; 435/68; 435/91; 435/172.1; 435/206; 435/253; 435/317; 435/840; 435/843; 435/259; 935/55; 935/56; 935/72

[58] Field of Search ............... 435/91, 172.3, 172.1, 435/253, 317, 840, 843, 267, 270, 259, 106–115, 206; 935/55, 56

[56] References Cited

U.S. PATENT DOCUMENTS 4,237,224 12/1980 Cohen et al. ......................... 435/91
4,346,169 8/1982 Akashi et al. ...................... 435/843

OTHER PUBLICATIONS

*Bergey's Manual of Determinative Bacteriology,* Buchanan et al (ed.), 1974, Williams & Wilkins Co., Baltimore, pp. 599–600.
*Molecular Breeding and Genetics of Applied Microorganisms,* Sakaguchi et al (ed.), 1980, Academic Press, New York, pp. 85–88.

*Primary Examiner*—James Martinell
*Attorney, Agent, or Firm*—Antonelli, Terry & Wands

[57] ABSTRACT

A novel lysozyme-sensitive microorganism belonging to the genus Corynebacterium or Brevibacterium and having a sensitivity to lysozyme at a concentration of less than 25 µg/ml is provided from selected mutants. This novel microorganism is especially suitable for use in recombinant DNA technology.

5 Claims, No Drawings

NOVEL LYSOZYME-SENSITIVE MICROORGANISM

This is a continuation of application Ser. No. 372,129, filed Apr. 27, 1982 now abandoned.

BACKGROUND OF THE INVENTION

The present invention relates to a novel lysozyme-sensitive microorganism belonging to the genus Corynebacterium or Brevibacterium, a process for preparing a protoplast from the microorganism, a process for transforming the microorganism, a process for using the microorganism as a host in recombinant DNA technology, and an obtained transformant.

Lysozyme-sensitive microorganisms belonging to the genus Corynebacterium or Brevibacterium have been known (Japanese Published Unexamined Patent Application No. 122794/79, etc.). However, the microorganisms of the present invention are more lysozyme-sensitive than those of the Japanese Patent Application, and therefore useful for gene engineering study as hereinafter described.

DETAILED DESCRIPTION OF THE INVENTION

The present novel lysozyme-sensitive microorganism is a microorganism belonging to the genus Corynebacterium or Brevibacterium and having a sensitivity to lysozyme at a concentration of less than 25 μg/ml. The microorganism of the present invention can be converted to protoplast by treating it only with lysozyme under a hypertonic condition to remove the cell wall, without pretreatment with a drug such as an antibiotic during growth.

Recently, genetic engineering technology of inserting a foreign gene in plasmid or phage DNA in vitro and introducing the resultant recombinant DNA into host cells have attracted attention.

The transformants obtained by this technology are important as a means to produce the foreign DNA by the autonomous replication of the recombinant DNA and to endow the cell with valuable properties due to the presence of the foreign DNA.

Most of the researches in this art have been carried out using *Escherichia coli* as a host, and attempts have also been made to establish "recombinant DNA technology" using other industrially important microorganisms than *Escherichia coli*, such as *Bacillus subtilis* capable of producing amylase, etc., actinomyces capable of producing antibiotics, etc., yeasts capable of producing alcohol, etc.

In genetic engineering, it is necessary to isolate plasmids for preparation of vector and analysis of a hybrid plasmid wherein foreign DNA is inserted. To this end cells must be ruptured at first. The rupture must be carried out under a mild condition to avoid shearing of DNA. Thus, mechanical rupturing such as ultrasonication and French press is unapplicable, and usually a procedure using cell wall-lytic enzyme is used. Lytic enzymes suitable for each of the aforesaid microbial species on which research of recombinant DNA is made have been known and are used.

The cell walls of bacteria such as *Escherichia coli* or *Bacillus subtilis* can be readily removed with lysozyme, i.e. an enzyme capable of lysing cell walls of bacteria. However, there are some bacteria whose cell walls are hardly lysed with lysozyme. For these bacteria, such a procedure has been used that the bacterium is contacted with a high concentration of an amino acid such as glycine or with an antibiotic such as penicillin during growth to render cells lysozyme-sensitive, and the resulting bacterium is treated with lysozyme.

The bacteria species belonging to the genus Corynebacterium or Brevibacterium, which are used in industrial production of various amino acids such as glutamic acid and lysine, usually have cell walls that are resistant to lysozyme. Therefore, such a procedure for removing the cell walls as mentioned above has been so far used for these bacteria species, that is, the cells are treated first with an antibiotic such as penicillin during the growth and then with lysozyme. However, the procedure is complicated and has an additional disadvantage that the regenerating ability of the resulting protoplast is low.

To establish a recombinant DNA technology in the useful bacteria such as those belonging to the genus Corynebacterium or Brevibacterium, the present inventors have been investigating processes for removing the cell walls of these bacteria. The present inventors studied a process for removing cell walls with lysozyme, using lysozyme-sensitive strains of the bacteria species belonging to the genus Corynebacterium or Brevibacterium disclosed in Japanese Published Unexamined Patent Application No. 122794/79, 4293/80 or 42593/81. However, the cell walls of the strains were not removed with lysozyme without pretreatment with penicillin, etc. as in the case of the lysozyme-insensitive strains. As a result of further study, the present inventors have found that the cell walls of lysozyme-ultrasensitive strains, which have a much higher sensitivity to lysozyme than the lysozyme-sensitive strains disclosed in the above-mentioned Japanese Application, can be lysed with lysozyme without any pretreatment with penicillin, etc. Furthermore, the present inventors have found that plasmid can be easily extracted from these lysozyme-ultrasensitive cells, and the regenerating ability of protoplast formed by the lysozyme treatment is high, so that the transformation of the protoplast by DNA can be efficiently carried out. The present invention has been completed on the basis of these findings.

The lysozyme-sensitive strains of the present invention can be obtained by subjecting lysozyme-insensitive strains (for example, wild-type strains) or the lysozyme-sensitive strains of the genus Corynebacterium or Brevibacterium to mutation treatment (hereinafter, the lysozyme-sensitive strains of the present invention are referred to as "lysozyme-ultrasensitive strains"). The ordinary mutation procedures, for example, ultraviolet irradiation, γ-ray irradiation, chemical mutagenesis and the like can be used. In selecting lysozyme-ultrasensitive strains from mutagenized cells, it is necessary to select those which fail to grow in a medium containing lysozyme at a very low concentration (less than 25 μg/ml), in which the parent strains can fully grow, and which can grow in a medium containing no lysozyme.

Examples of the present microorganisms include L-15 strain (FERM P-5946) derived from *Corynebacterium glutamicum* 225-106 (FERM P-5945), L-103 strain (FERM P-5947) derived from *Corynebacterium herculis* ATCC 13868, L-204 strain (FERM P-5948) derived from *Brevibacterium divaricatum* ATCC 14020 and L-312 strain (FERM P-5949) derived from *Brevibacterium lactofermentum* ATCC 13655. These lysozyme-ultrasensitive strains were deposited with the Fermentation Research Institute and assigned the accession numbers mentioned above, and further deposited with the American Type Culture Collection, USA under the accession numbers ATCC 31834, 31866, 31867 and 31868, respectively.

The 225-106 strain named "*Corynebacterium glutamicum*" is a strain isolated from a soil sample and has the following bacteriological properties. Investigation of the bacteriological properties was conducted according to the procedure described in "Manual of Microbiological Methods" by the Society of American Bacteriologist Committee on Bacteriological Technique (1957).

I. Morphological characteristics of cells

Usually ellipsoidal or short rods of 0.7-1.0 by 1.0-3.0μ; Pleomorphic due to snapping division and branching cells; Gram positive; Non-motile; Non-spore-forming.

II. Culture characteristics on a rich nutrient medium

On an agar plate, a single, circular, lustrous and pale yellow colony; On a slant, a similar pale yellow opaque colony; On an agar stab, abundant growth on surface and slight growth in deep; In a liquid medium, slight growth and slightly flocculent sediment.

III. Physiological characteristics (1) Temperature: optimum temperature 25°-37° C.; growth occurs slightly at 42° C.
(2) pH : optimum pH 7-8; growth occurs at pH 6-9
(3) Thermal resistance: none
(4) Relation to free oxygen: aerobic
(5) Gelatin liquefaction: none
(6) Assimilation of casein: negative
(7) Indole production: none
(8) Catalase: positive
(9) Assimilation of starch: negative
(10) Acid production from glucose, fructose, mannose and maltose; non-acid production from xylose, galactose, lactose and glycerol
(11) Requirement of biotin: positive
(12) Glutamic acid is accumulated in a large quantity in a medium wherein the amount of biotin is restricted.
(13) Lactic acid and α-ketoglutaric acid are accumulated in a medium containing biotin in a high concentration.

These characteristics are compared with those of bacteria disclosed in J. Gen. Appl. Microbiol., 73, 279-301 (1967). Since the characteristics coincide well with those of *Corynebacterium glutamicum*, the 225-106 strain is identified as a strain of *Corynebacterium glutamicum*.

An example of a procedure for obtaining a lysozyme-ultrasensitive strain of the present invention from a lysozyme-insensitive or sensitive strain of the genus Corynebacterium or Brevibacterium is described below.

A parent strain is inoculated in a nutrient medium and cultured at 20°-35° C. with shaking. Culturing is discontinued in the course of the logarithmic growth phase. The cells are collected, washed with physiological saline solution and then suspended in an appropriate buffer solution (pH 5.5-8.0), for example, M/20 Tris-maleate buffer (pH 6.0) in a concentration of $1 \times 10^7 - 1 \times 10^9$ cells/ml. To the resulting suspension is added nitrosoguanidine in a final concentration of 200-500 μg/ml and the mixture is allowed to stand at 20°-35° C. for 30 minutes to 1 hour.

The cells are collected by centrifugation, washed with the same buffer and suspended in physiological saline solution. A certain amount of the suspension diluted with physiological saline solution is spread on a nutrient agar medium, for example, NB agar medium (medium containing 1.8% agar in NB medium which contains 20 g of bouillon powder and 5 g of yeast extract in 1 l of water). After incubation at 25°-35° C. for 1 to 4 days, the formed colonies are replicaplated to a nutrient agar medium and a nutrient agar medium containing 2.5-25 μg/ml lysozyme. The replica plates are incubated at 25°-35° C. for 1 to 4 days, and then those colonies which can grow on the nutrient agar medium but not on the nutrient agar medium containing lysozyme are kept as lysozyme-ultrasensitive mutants.

All the aforementioned lysozyme-ultrasensitive strains are obtained in this way.

The lysozyme-sensitivity of the lysozyme-ultrasensitive mutants can be determined by inoculating a drop of cell suspension containing about $10^4$ cells of the mutant in the logarithmic phase of growth on NB agar medium containing lysozyme in a series of two-fold dilution and by observing the growth after incubation at 30° C. for 2 days.

A minimal lysozyme concentration at which no growth of a given microorganism is observed is taken as a lysozyme sensitivity of the microorganism (minimum inhibitory concentration), and the comparison of sensitivity of the mutants with that of the respective parent strains are given in Table 1.

The lysozyme-ultrasensitive mutants of the present invention are obtained by selecting the strains unable to grow on the NB agar medium containing 2.5-25 μg/ml lysozyme, as described above, whereas the lysozyme-sensitive mutants of bacteria species belonging to the genus Corynebacterium or Brevibacterium disclosed in Japanese Published Unexamined Patent Application No. 122794/79, were obtained by selecting the strains unable to grow on the NB agar medium containing 200-400 μg/ml lysozyme. Thus, these two seem to have a possibility of being essentially different in properties. Although the lysozyme sensitivity of the parent strains used in these two experiments as measured by the method described above are almost comparable, between 400 and 800 μg/ml, that of the resultant mutants differ considerably. That is, the sensitivities of the mutants of the present invention is 1.6-3.2 μg/ml, whereas that of the mutants of the Japanese Patent Application is 25-400 μg/ml. Furthermore, as will be explained below, the lysozyme-ultrasensitive mutants of the present invention have advantages due to the high lysozyme susceptibility of their cell walls, which can be lysed without pretreatment with penicillin, whereas the lysozyme-sensitive mutants of the Japanese Patent Application have no such characteristics. Thus, it is apparent that the lysozyme-ultrasensitive strains are distinct from the lysozyme-sensitive strains.

TABLE 1

| Strains | FERM P | ATCC | Lysozyme sensitivity, minimum inhibitory concentration (MIC, μg/ml) |
|---|---|---|---|
| *Corynebacterium glutamicum* 225-106 | 5945 | 31833 | 800 |
| *Corynebacterium glutamicum* L-15 | 5946 | 31834 | 3.2 |
| *Corynebacterium herculis* ATCC 13868 | — | | 400 |
| *Corynebacterium herculis* L-103 | 5947 | 31866 | 3.2 |
| *Brevibacterium divaricatum* ATCC 14020 | — | | 800 |
| *Brevibacterium divaricatum* L-204 | 5948 | 31867 | 1.6 |
| *Brevibacterium* | — | | 400 |

TABLE 1-continued

| Strains | FERM P | ATCC | Lysozyme sensitivity, minimum inhibitory concentration (MIC, μg/ml) |
|---|---|---|---|
| lactofermentum ATCC 13655 | | | |
| Brevibacterium lactofermentum L-312 | 5949 | 31868 | 3.2 |

The usefulness of the present microorganisms whose cell walls can be easily lysed and removed by lysozyme resides in that (1) efficient transformation of protoplast by DNA is possible due to the high regenerating ability of the protoplast and (2) extraction of DNA such as plasmid from the cells can be easily made.

The transformation and the extraction are described in detail below.

(1) Preparation of protoplast from the lysozyme-ultrasensitive mutants and transformation of the protoplast by DNA Protoplast can be prepared by treating the cultured cells only with lysozyme. Any medium wherein the present microorganism propagates may be used. For example, NB medium can be used. Microorganisms are inoculated onto a medium and cultured at 25°–37° C. with shaking up to the middle to the late of the logarithmic phase of growth. The cells are collected and suspended in an appropriate hypertonic medium containing 0.2–10 mg/ml lysozyme. An example of the hypertonic medium is PFM medium containing 0.4 M sucrose and 0.01 M $MgCl_2 \cdot 6H_2O$ in two-fold diluted SSM medium and being adjusted to pH 7.0–8.5. The SSM medium consists of 20 g of glucose, 10 g of $(NH_4)_2SO_4$, 3 g of urea, 1 g of yeast extract, 1 g of $KH_2PO_4$, 0.4 g of $MgCl_2 \cdot 6H_2O$, 10 mg of $FeSO_4 \cdot 7H_2O$, 0.2 mg of $MnSO_4 \cdot 4-6H_2O$, 0.9 mg of $ZnSO_4 \cdot 7H_2O$, 0.4 mg of $CuSO_4 \cdot 5H_2O$, 0.09 mg of $Na_2B_4O_7 \cdot 10H_2O$, 0.04 mg of $(NH_4)_6Mo_7O_{24} \cdot 4H_2O$, 30 μg of biotin, and 1 mg of thiamine hydrochloride in 1 l of water and is adjusted to pH 7.2. Normal cells are gradually converted to protoplast during incubation at 30°–37° C., and the degree of the conversion can be monitored under an optical microscope. The time necessary for the conversion of most of the cells to protoplast depends upon the strain used, and usually is 0.5–8 hours under the above-mentioned condition. After the lysozyme treatment, the amount of the normal cells resistant to hypotonic condition is less than $10^{-4}$ of the initial amount of the normal cells subjected to the lysozyme treatment.

The protoplast thus prepared has an ability to form colonies (regenerating ability) on a hypertonic agar medium. An example of a hypertonic agar medium is a medium containing 13 g/l agar in RCGP medium [a medium containing 5 g of glucose, 5 g of casein hydrolyzate, 2.5 g of yeast extract, 3.5 g of K, 1.5 g of KH, 0.41 g of $MgCl_2 \cdot 6H_2O$, 10 mg of $FeSO_4 \cdot 7H_2O$, 2 mg of $MnSO_4 \cdot 4-6H_2O$, 0.9 mg of $ZnSO_4 \cdot 7H_2O$, 0.04 mg of $(NH_4)_6Mo_7O_{24} \cdot 4H_2O$, 30 μg of biotin, 2 mg of thiamine hydrochloride, 135 g of disodium succinate, and 30 g of polyvinylpyrrolidone (molecular weight: 10,000) in 1 l of water and being adjusted to pH 7.2]. Regeneration of protoplast on RCGP agar medium depends upon the strain used, and the concentration and time of lysozyme treatment, and the efficiency of regeneration is usually 20–70% on the basis of the initial amount of the normal cells subjected to the lysozyme treatment. The time required for observable regeneration of colonies depends upon the strain used, and it usually takes 5–7 days for the colonies to become large enough to pick up.

Transformation of the protoplast obtained from the microorganisms having the above-mentioned characteristics is carried out by mixing the protoplast with DNA under a hypertonic condition where polyethyleneglycol (PEG) or polyvinyl alcohol (PVA), and a divalent metal cation coexist.

Transformants can be obtained as normal cells by regenerating the protoplast on a hypertonic agar medium such as RCGP agar medium in the same manner as in the regeneration of the protoplast mentioned above. Transformants can be selected on the basis of phenotypic properties which genes on the introduced DNA provides. The selection can be carried out on a hypertonic agar medium simultaneously with the regeneration, or after the regeneration.

In the transformation of the protoplast by plasmid DNAs according to the foregoing procedure, transformant can be obtained with a frequency of $10^{-4} - 10^{-6}$ per regenerated cell.

Transformation is described in detail in the examples shown below.

(2) Isolation of plasmid DNA from transformant

The microorganism is cultured in a medium suitable for propagation of the microorganism, for example, NB medium, collected and treated with lysozyme to lyse the cell walls. Plasmid can be easily isolated from the lysate according to the ordinary procedure as described, for example, in Biochim. Biophys. Acta 383 457–463 (1975).

Suitable concentration of lysozyme depends upon the strain used, and is usually 0.1–10 mg/ml.

Application of recombinant DNA technique to the bacteria species of the genera Corynebacterium and Brevibacterium, which are used in the industrial production of various amino acids such as glutamic acid, lysine, etc., has such a possibility that genes taking part in biosynthesis of useful substances such as amino acid, etc. from these bacteria and other microorganisms can be cloned to intensify the biosynthetic activities by the amplification of the genetic information, thereby increasing the production of useful substances. Also the genes of animal and plant can be cloned, so that useful polypeptides can be produced in these bacteria species by the expression of the genetic information. Thus the application has tremendus industrial importances. The lysozyme-ultrasensitive microorganisms of the present invention enable extractive separation of DNA such as plasmid, etc. from the cells and transformation of the cells by DNA, and therefore can facilitate application of recombinant DNA technique to the genera Corynebacterium and Brevibacterium.

The present inventors have further found that the microorganisms of the present invention are useful as safe host microorganisms in the recombinant DNA technology.

It is prerequisite for recombinant DNA technique to establish a safe host-vector system. It requires a very weak pathogenicity, no parasistic ability to human and rapid loss of viability when released in the environment. *Escherichia coli*, the first host in the technology, is a parasite to human by nature, and its safety has long been discussed. However, at least strain K-12 cultured in laboratories for a long period of time was found to have a considerably reduced parasitic tendency and pathogenicity and has been approved as B 1 host. It is reported that, when the K-12 strain was administered into human bodies, the microorganism can be recovered from the bodies over a period of a few days with an overall recovery of about 1% [Science 209 391–394 (1980)].

In extending the recombinant DNA technique to microorganisms capable of producing amino acids, nucleic acids, antibiotics, etc., it is necessary to establish safe host-vector system. Most of the relevant microorganisms are isolated from soils and thus their parasitic ability to human bodies is regarded as low, but some may survive the conditions prevailing in the digestive tract of human body, though not colonizing it, and might be recovered alive. To increase the safety of such strains, a nature of being perishable in the digestive tract can be artificially endowed to the strains. In the case of B 2 host, such a weak nature as being perishable when released in the environment has been endowed.

It has been found that the lysozyme-ultrasensitive microorganisms of the present invention are much more readily perishable in digestive tracts of animals, when tested therein. That is, the microorganisms shown in Table 2 were orally administered at a dose of about $3-5 \times 10^9$ per male ddY mouse (body weight: 19 g±1), each group consisting of two mice. The number of microorganisms remaining in the intestines and the number of microorganisms discharged into feces were measured by spreading appropriately diluted 10% homogenates each thereof on NB plate medium. As is apparent from Table 2, the lysozyme-ultrasensitive microorganisms of the present invention are considerably perished and discharged, as compared with the parent strains, and the number of the microorganisms remaining in the intestines is also more rapidly decreased.

TABLE 2

| Micro-organisms used | Recovery % | | | |
|---|---|---|---|---|
| | In feces | | In intestines | |
| | *hours 0–20.5 | hours 20.5–43.5 | **hours 20.5 | hours 43.5 |
| Corynebacterium glutamicum 225-106 | 53.8 | 0.08 | $5.7 \times 10^{-7}$ | $<9 \times 10^{-10}$ |
| Corynebacterium glutamicum L-15 | 4.3 | $<9.3 \times 10^{-9}$ | $<1.3 \times 10^{-9}$ | $<8.7 \times 10^{-10}$ |
| Corynebacterium herculis ATCC 13868 | 44.5 | 0.05 | $4.6 \times 10^{-7}$ | $<8.5 \times 10^{-10}$ |
| Corynebacterium herculis L-103 | 3.4 | $<8.7 \times 10^{-9}$ | $<1 \times 10^{-9}$ | $<7.3 \times 10^{-10}$ |
| Corynebacterium divaricatum ATCC 14020 | 57.2 | 0.09 | $6.4 \times 10^{-7}$ | $<8.7 \times 10^{-10}$ |
| Corynebacterium divaricatum L-204 | 7.4 | $<8.9 \times 10^{-9}$ | $<1.1 \times 10^{-9}$ | $<9.1 \times 10^{-10}$ |
| Brevibacterium lactofermentum ATCC 13655 | 64.5 | 0.1 | $4.3 \times 10^{-7}$ | $<8.2 \times 10^{-9}$ |
| Brevibacterium lactofermentum L-312 | 5.6 | $<7.4 \times 10^{-6}$ | $<8.4 \times 10^{-9}$ | $<2.3 \times 10^{-9}$ |

*Time after the administration of the relevant microorganism. Column "0-20.5" shows the recovery of microorganisms (% of the given microorganisms) in total feces from zero hour (the time of administration) up to 20.5 hours.
**Column "20.5 hours" shows the recovery of microorganisms in the intestine removed from mice at 20.5 hours.

The present inventors have studied the sensitivities of a lysozyme-ultrasensitive strain toward various drugs. A drop of the cell suspension corresponding to about $10^4$ cells in the logarithmic phase of growth is inoculated on NB agar medium containing a test drug in a series of two-fold dilution. After incubation at 30° C. for 2 days, the growth of each inoculum was scored. As shown in Table 3, it was found that the strain L-15 is more sensitive to penicillin, rifampicilin and of course to lysozyme than its parent 225-106. This suggests that these lysozyme-ultrasensitive strains are more readily killed or inhibited from growing than their parents, and therefore the antibiotic resistance conferred to host cells by plasmid vectors will be counterbalanced.

TABLE 3

| | Sensitivity to drugs (*MIC, µg/ml) | | |
|---|---|---|---|
| | lysozyme | penicillin G | rifampicilin |
| Corynebacterium glutamicum 225-106 | 800 | 0.12 | 0.016 |
| Corynebacterium glutamicum L-15 | 3.2 | 0.015 | 0.004 |

*MIC: Minimum inhibitory concentration

As described above, the present lysozyme-ultra-sensitive microorganisms are considerably perishable in the digestive tracts of animals, and are highly sensitive to various drugs. This shows that the present microorganisms are preferable as a host microorganism for recombinant DNA.

EXAMPLE 1

Corynebacterium glutamicum 225-106, Corynebacterium herculis ATCC 13868, Brevibacterium divaricatum ATCC 14020, and Brevibacterium lactofermentum ATCC 13655 are inoculated in NB medium (pH 7.2), and cultured at 30° C. with shaking. The growth is terminated in the middle of the logarithmic phase of growth, and cells are collected, washed with physiological saline solution, and then suspended in M/20 Tris-maleate buffer (pH 6.0) to make about $5 \times 10^8$ cell/ml.

The suspensions are mixed with nitrosoguanidine to make a final concentration of 400 µg/ml, and allowed to stand at 25° C. for 30 minutes. The cells are collected by centrifugation, washed with the same buffer, and then suspended in physiological saline solution. The suspension is appropriately diluted with the saline and spread on NB-agar medium. Incubation is carried out at 30° C. for 2 days and the resultant colonies are replica-plated to NB-agar medium with or without 12.5 µg/ml lysozyme (egg white, 6×crystallized, made by Seikagaku Kogyo Co., Ltd.). The replica-plates are incubated at 30° C. for 2 days and then those colonies which can grow on the NB medium but not on the NB medium containing lysozyme are kept as lysozyme-ultrasensitive mutants.

TABLE 4

| Parent strains | Lysozyme-ultrasensitive mutant strains |
|---|---|
| Corynebacterium glutamicum 225-106 | Corynebacterium glutamicum L-15 |
| Corynebacterium herculis ATCC 13868 | Corynebacterium herculis L-103 |
| Brevibacterium divaricatum ATCC 14020 | Brevibacterium divaricatum L-204 |
| Brevibacterium lactofermentum ATCC 13655 | Brevibacterium lactofermentum L-312 |

EXAMPLE 2

Lysis and removal of cell walls of the microorganisms of the present invention by lysozyme and regeneration of protoplast formed.

Seed cultures of *Corynebacterium glutamicum* 225-106, *Corynebacterium herculis* ATCC 13868, *Brevibacterium devaricatum* ATCC 14020, *Brevibacterium lactofermentum* ATCC 13655, and the lysozyme-ultrasensitive mutant strains obtained in Example 1 by derivation therefrom are respectively inoculated onto NB medium and cultured at 30° C. with shaking. Absorbancy (OD) at 660 nm is measured with a colorimeter made by Tokyo Koden Co. A small portion of the culture is appropriately diluted with physiological saline solution when OD reaches 0.6. An aliquot of the diluted solution is spread onto NB agar medium to determine the cell number. At the same time cells are harvested from the culture broth and suspended in a medium (pH 7.6) containing 1 mg/ml lysozyme in RCGP medium to make the cell density about $10^9$ cells/ml. The suspension is transferred to an L-shaped test tube and incubated at 30° C. with gentle shaking.

Five hours thereafter, cells are recovered by centrifugation at $2,500 \times G$ for 10 minutes, suspended in PFM medium, twice washed by centrifugation and resuspended in PFM medium to prepare protoplast suspension. A portion of the suspension is appropriately diluted with RCGP medium, and spread onto RCGP agar medium, while another portion is appropriately diluted with physiological saline solution, and spread onto NB agar medium. They are cultured at 30° C. to determine the number of colony-forming cells under the hypertonic condition as well as under the hypotonic condition. The number of colonies formed under the hypotonic condition is measured on the second day of culture (the number is no more increased with further incubation). The number of colonies formed under the hypertonic condition is measured on the seventh day of the culture after which the number of regenerated colonies is increased no more. The results are shown in Table 5.

TABLE 5

| Strains | Number of lysozyme-treated cells (cfu/ml) | Number of colony-forming cells after lysozyme treatment | |
|---|---|---|---|
| | | Hypotonic | Hypertonic |
| Corynebacterium glutamicum L-15 | $1.8 \times 10^9$ | $9.8 \times 10^3$ | $6.7 \times 10^8$ |
| Corynebacterium glutamicum 225-106 | $2.3 \times 10^9$ | $2.1 \times 10^9$ | $2.3 \times 10^9$ |
| Corynebacterium herculis L-103 | $1.2 \times 10^9$ | $6.5 \times 10^4$ | $2.4 \times 10^8$ |
| Corynebacterium herculis ATCC 13868 | $1.3 \times 10^9$ | $1.3 \times 10^9$ | $1.4 \times 10^9$ |
| Brevibacterium divaricatum L-204 | $9.6 \times 10^8$ | $1.1 \times 10^3$ | $6.4 \times 10^8$ |
| Brevibacterium divaricatum ATCC 14020 | $1.2 \times 10^9$ | $1.3 \times 10^9$ | $1.4 \times 10^9$ |
| Brevibacterium lactofermentum L-312 | $1.0 \times 10^9$ | $1.4 \times 10^4$ | $5.3 \times 10^8$ |
| Brevibacterium lactofermentum ATCC 13655 | $1.1 \times 10^9$ | $9.9 \times 10^8$ | $1.0 \times 10^9$ |

With all the parent strains, no formation of spherical protoplast is observed and only normal cells in the short rod form are observed under a microscope after they are subjected to action of lysozyme. The number of colonies formed under the hypotonic condition is not substantially different before and after the lysozyme treatment. On the other hand, the lysozyme-ultrasensitive strains are converted to protoplast by the action of lysozyme, and the ratio of the cells capable of forming colonies under the hypotonic condition where the protoplast is killed by rupture (osomotic-resistant normal cells) is $10^{-4} - 10^{-6}$ per cell subjected to the lysozyme treatment. These protoplasts can form colonies under a hypertonic condition, and their regeneration efficiency is 20-70% of the number of the cells subjected to lysozyme treatment. Cells from the regenerated colonies are normal so that they can grow on NB agar medium.

EXAMPLE 3

Transformation of the protoplasts prepared from the microorganisms of the present invention by plasmid pCG4 DNA (1) Preparation of plasmid pCG4

Plasmid pCG4 for use in transformation in the present Example is extracted from the cultured cells of *Corynebacterium glutamicum* 225-250 (FERM P-5939), a microorganism carrying pCG4, in the following manner.

Five milliliters of seed culture of *Corynebacterium glutamicum* 225-250 in NB medium is inoculated into 400 ml of SSM medium. Culturing is carried out at 30° C. with shaking. Optical density (OD) at 660 nm is measured with. Tokyo Koden colorimeter and at OD 0.2 penicillin G is added to the broth in a final concentration of 0.5 U/ml. Further, growth is continued at 30° C. to OD about 0.6.

Cells are recovered from the culture broth, washed with TES buffer (pH 8.0) consisting of 0.03M tris(hydroxymethyl)aminomethane (Tris), 0.005M EDTA and 0.05M NaCl and suspended in a lysozyme solution (pH 8.0) consisting of 25% sucrose, 0.1M NaCl, 0.05M Tris and 0.8 mg/ml lysozyme to make 10 ml of a suspension. The suspension is incubated at 37° C. for 4 hours. Then, 2.4 ml of 5M NaCl, 0.6 ml of 0.5M EDTA (pH 8.5) and 4.4 ml of a solution containing 4 g sodium laurylsulfate and 0.7M NaCl are added successively to the reaction suspension. After the mixture is stirred slowly, it is kept on an ice water bath for 15 hours. The whole lysate is put into a centrifugation tube and centrifuged under 69,400×g at 4° C. for 60 minutes to obtain a supernatant fluid. To the supernatant is added 10% by weight of polyethyleneglycol 6,000. After the mixture is stirred slowly to dissolve it, it is kept on an ice water bath. After 16 hours, the mixture is subjected to centrifugation under 1,500×g for 10 minutes to obtain a pellet. The pellet is redissolved in 5 ml of TES buffer and 2.0 ml of 1.5 mg/ml ethidium bromide is added. Cesium chloride is added to the mixture to adjust the density to 1.580. The solution is subjected to centrifugation under 105,000×g at 18° C. for 48 hours. After the density gradient centrifugation, a circular DNA closed with covalent bond is detected by UV irradiation as a high density band located in the lower part of the centrifugation tube. The band is taken out from the side of the tube with an injector to obtain a fraction containing plasmid pCG4. To remove ethidium bromide, the fraction is treated five times with an equal amount of cesium chloride saturated isopropyl alcohol solution consisting of 90% by volume of isopropyl alcohol and 10% TES buffer. Then, the residue is subjected to dialysis against TES buffer. Thus, 15 μg of plasmid pCG4 is obtained.

Plasmid pCG4 is a novel plasnid having a molecular weight of about 19 megadaltons, carrying genes for resistance to streptomycin and spectinomycin and having 4, 7, 9, 6 and 6 restriction sites for Eco RI, Bam HI, Hind III, Pst I and Sal I respectively.

(2) Transformation of the protoplast with plasmid pCG4

The lysozyme treated cells prepared in the same manner as in Example 2 are transformed with pCG4. Zero point five milliliters of protoplast suspension is taken into a small test tube, centrifuged at 2,500×G for 5 minutes. The precipitate is resuspended in 1 ml of TSMC buffer (10 mM magnesium chloride, 30 mM calcium chloride, 50 mM Tris, 400 mM sucrose : pH 7.5) and washed by centrifugation. The precipitated protoplast is resuspended in 0.1 ml of TSMC buffer with gentle shaking.

To the suspension is added 0.1 ml of a DNA solution containing 0.2 μg of DNA which is prepared by diluting a pCG4 solution two-folds with two-folds concentrated TSMC buffer and the resultant mixture is stirred. Then, 0.8 ml of a solution containing 20% polyethylene glycol 6,000 in TSMC buffer is added to the mixture and the resultant mixture is gently stirred. Three minutes thereafter, the suspension is mixed with 2 ml of RCGP medium, and centrifuged at 2,500×G for 5 minutes to remove the supernatant. The precipitated protoplast is suspended in 1 ml of RCGP medium, diluted to several levels with RCGP medium, and spread onto an RCGP agar medium containing 400 μg/ml of spectinomycin. To determine the number of colony-forming cells, the protoplast suspension is highly diluted, spread onto an RCGP agar medium without spectinomycin and incubated at 30° C. for 6 days.

The colonies formed on the RCGP medium containing spectinomycin is plated onto an NB agar medium containing 12.5 μg/ml of streptomycin and cultured at 30° C. for 2 days to investigate cross resistance to spectinomycin and streptomycin. The strains showing the cross resistance are selected at random, and plasmid is isolated according to the procedure shown in Example 4.

The results are summarized in Table 6.

TABLE 6

| Recipient microorganism | Frequency of appearance of spectinomycin-resistant cells* | Properties of spectinomycin-resistant cells** | |
|---|---|---|---|
| | | Streptomycin cross resistance | Presence of pCG4 |
| Corynebacterium glutamicum 225-106 | 1.7 × 10$^{-7}$ | − (5/5) | − (2/2) |
| Corynebacterium glutamicum L-15 | 2.4 × 10$^{-3}$ | + (50/50) | + (2/2) |
| Corynebacterium herculis ATCC 13868 | <1.3 × 10$^{-7}$*** | | |
| Corynebacterium herculis L-103 | 7.5 × 10$^{-4}$ | + (50/50) | + (2/2) |
| Brevibacterium divaricatum ATCC 14020 | 3.5 × 10$^{-7}$ | − (5/5) | − (2/2) |
| Brevibacterium divaricatum L-204 | 1.0 × 10$^{-6}$ | + (50/50) | + (2/2) |
| Brevibacterium lactofermentum ATCC 13655 | 3.1 × 10$^{-7}$ | − (5/5) | − (2/2) |
| Brevibacterium lactofermentum L-312 | 2.4 × 10$^{-6}$ | + (50/50) | + (2/2) |

*Frequency per colony-forming microorganism (regenerated microorganism) under a hypertonic condition.
**The number of cells tested (denominator) and those of negative (−) or positive (+) cells (numerator) are illustrated in parentheses.
***Spectinomycin-resistant cells are not obtained from the strain.

The spectinomycin-resistant strains obtained by treating lysozyme-insensitive strains with lysozyme and pCG4 plasmid show no streptomycin cross resistance, and pCG4 is not detected in these spectinomycin-resistant strains by the isolation procedure used for the strain 225-250. On the other hand, the spectinomycin-resistant strains obtained by treating lysozyme-ultrasensitive strains with lysozyme and pCG4 plasmid have streptomycin cross resistance, and the plasmid isolated from these strains give the same DNA fragments upon digestion with restriction endonuclease Hind III as those from pCG4.

The FERM P numbers of the transformants thus obtained are shown in Table 7.

TABLE 7

| Recipient strain | pCG4 transformant | PERM P | ATCC |
|---|---|---|---|
| Corynebacterium glutamicum L15 | L15/pCG4 | 5950 | 31835 |
| Corynebacterium herculis L103 | L103/pCG4 | 5951 | 31869 |
| Brevibacterium divaricatum L204 | L204/pCG4 | 5952 | 31870 |
| Brevibacterium lactofermentum L312 | L312/pCG4 | 5953 | 31871 |

EXAMPLE 4

Isolation of pCG4 plasmid from the cells transformed with pCG4

Five milliliters of seed culture in NB medium of each pCG4 transformant obtained in Example 3, Corynebacterium glutamicum L15/pCG4, Corynebacterium herculis L103/pCG4, Brevibacterium divaricatum L204/pCG4 or Brevibacterium lactofermentum L312/pCG4 is inoculated in 400 ml of NB medium and cultured with shaking at 30° C. for 12 hours.

The cells are collected from the culture broth, washed with TES buffer, suspended in 10 ml of a lysozyme solution (25% sucrose, 0.1M NaCl, 0.05M Tris, 0.8 mg/ml lysozyme : pH 8) and subjected to incubation at 37° C. for one hour. Then the reaction solution is successively admixed with 2.4 ml of 5M NaCl, 0.6 ml of 0.5M EDTA (pH 8.5) and 4.4 ml of a solution containing 4% sodium laurylsulfate and 0.7M NaCl, gently mixed, and placed in ice water for 15 hours. The whole lysate is transferred into a centrifugation tube, and subjected to centrifugation at 69,400×G at 4° C. for 60 minutes to obtain the supernatant fraction. Polyethylene glycol 6000 is added to the supernatant to make the final concentration 10% (W/W) with gentle stirring and the resultant solution is placed in ice water. Sixteen hours thereafter, pellets are recovered by centrifugation at 1,500×G for 10 minutes, and dissolved in 5 ml of TES buffer. The solution is admixed with 2 ml of 1.5 mg/ml ethidium bromide and then with cesium chloride to make a density of 1.580. The solution is subjected to density gradient centrifugation under the same conditions as described in Example 3 to separate plasmid. The fraction containing pCG4 is treated with the isopropyl alcohol solution in the same manner as in Example 3 to extract and remove ethidium bromide, and dialyzed against the TES buffer.

In this manner, 15–30 μg of pCG4 DNA was obtained from all the lysozyme-ultrasensitive strains containing pCG4.

What is claimed is:

1. A biologically pure culutre of a novel lysozyme-sensitive microorganism obtained by mutation treatment of a microorganism belonging to the genus Corynebacterium or Brevibacterium, having a sensitivity to lysozyme, having the ability to be converted to protoplast by treatment with lysozyme to remove the cell wall without pretreatment with an antibiotic and having an efficient transformation ability due to the high regenerating ability of the protoplast, wherein the lysozyme-sensitive microorganism is selected from the group consisting of *Corynbacterium glutamicum* L-15 (FERM P-5946, ATCC 31834), *Corynebacterium hercules* L-103 (FERM P-5947, ATCC 31866), *Brevibacterium divaricatum* L-204 (FERM P-5948, ATCC 31867) and *Brevibacterium lactofermentum* L-312 (FERM P-5949, ATCC 31868).

2. A process for preparing a protoplast of a microorganism belonging to the genus Corynbascterium or Brevibacterium, which comprises treating a lysozyme-sensitive microorganism obtained by mutation treatment of a microorganism belonging to the genus Corynebacterium or Brevibacterium, having a sensitivity to lysozyme, having the ability to be converted to protoplast by treatment with lysozyme to remove the cell wall without pretreatment with an antibiotic and having an efficient transformation ability due to the high regenerating ability of the protoplast, with lysozyme to form a protoplast of the microorganism, wherein the lysozyme-sensitive microorganism is selected from the group consisting of *Corynbacterium glutamicum* L-15 (FERM P-5946, ATCC 31834), *Corynbacterium herculis* L-103 (FERM P-5947, ATCC 31866), *Brevibacterium divaricatum* L-204 (FERM P-5948, ATCC 31867) and *Brevibacterium lactofermentum* L-312 (FERM P-5949, ATCC 31868).

3. A process for transforming a microorganism belonging to the genus Corynbascterium or Brevibacterium, which comprises treating a microorganism obtained by mutation treatment of a microorganism belonging to the genus Corynebacterium or Brevibacterium, having a sensitivity to lysozyme, having the ability to be converted to protoplast by treatment with lysozyme to remove the cell wall without pretreatment with an antibiotic and having an efficient transformation ability due to the high regenerating ability of the protoplast with lysozyme; introducing deoxyribonucleic acid into the protoplast; and regenerating the protoplast to normal cells, wherein the lysozyme-sensitive microorganism is selected from the group consisting of *Corynbacterium glutamicum* L-15 (FERM P-5946, ATCC 31834), *Corynebascterium herculis* L-103 (FERM P-5947, ATCC 31866), *Brevibacterium divaricatum* L-204 (FERM P-5948, ATCC 31867) and *Brevibacterium lactofermentum* L-312 (FERM P-5949, ATCC 31868).

4. A process which comprises using a microorganism obtained by mutation treatment of a microorganism belonging to the genus Corynebacterium or Brevibacterium, having a sensitivity to lysozyme, having the ability to be converted to protoplast by treatment with lysozyme to remove the cell wall without pretreatment with an antibiotic and having an efficient transformation ability due to the high regenerating ability of the protoplast, as a host in introducing a DNA into the microorganism, wherein the lysozyme-sensitive microrganism is selected from the group consisting of *Corynbacterium glutamicum* L-15 (FERM P-5946, ATCC 31834), *Corynebacterium herculis* L-103 (FERM P-5947, ATCC 31866), *Brevibacterium divaricatum* L-204 (FERM P-%(48, ATCC 31867) and *Brevibacterium lactofermentum* L-312 (FERM P-5949, ATCC 31868).

5. A biologically pure culture of a novel lysozyme-sensitive microorganism obtained by mutation treatment of a microroganism belonging to the genus Corynbacterium or Brevibacterium, having a sensitivity to lysozyme, having the ability to be converted to protoplast by treatment with lysozyme to remove the cell wall without pretreatment with an antibiotic and having an efficient transformation ability due to the high regenerating ability of the protoplast, and carrying pCG4 plasmid, wherein the lysozyme-sensitive microorganism is selected from the group consisting of *Corynebacterium glutamicum* L-15/pCG4 (FERM P-5950, ATCC 31835), *Corynbacterium herculis* L-103/pCG4 (FERM P-5951, ATCC 31869), *Brevibacterium divaricatum* L-204/pCG4 (FERM P-5952, ATCC 31870) and *Brevibacterium lactofermentum* L-312/pCG4 (FERM P-5953, ATCC 31871).

* * * * *